US007655690B2

(12) United States Patent
Merce Vidal et al.

(10) Patent No.: US 7,655,690 B2
(45) Date of Patent: Feb. 2, 2010

(54) 1-SULFONYLINDOLE DERIVATIVES, THEIR PREPARATION AND THEIR USE AS 5-HT$_6$ LIGANDS

(75) Inventors: Ramon Merce Vidal, Barcelona (ES); Xavier Codony Soler, Mataro (ES); Alberto Dordal Zueras, Barcelona (ES)

(73) Assignee: Laboratorios del Dr. Esteve S.A., Barcelona (ES)

( * ) Notice: Subject to any disclaimer, the term of this patent is extended or adjusted under 35 U.S.C. 154(b) by 368 days.

(21) Appl. No.: 10/566,400

(22) PCT Filed: Jul. 29, 2004

(86) PCT No.: PCT/EP2004/008516

§ 371 (c)(1),
(2), (4) Date: Oct. 10, 2006

(87) PCT Pub. No.: WO2005/013974

PCT Pub. Date: Feb. 17, 2005

(65) Prior Publication Data

US 2007/0060581 A1    Mar. 15, 2007

(30) Foreign Application Priority Data

Jul. 30, 2004   (ES)   ............... 200301806

(51) Int. Cl.
*A61K 31/415*   (2006.01)
*C07D 209/04*   (2006.01)
(52) U.S. Cl. ..................... 514/415; 548/469
(58) Field of Classification Search ............ 548/465, 548/469; 514/415
See application file for complete search history.

(56) References Cited

U.S. PATENT DOCUMENTS

| 5,382,670 | A | 1/1995 | Summers et al. |
| 6,187,805 | B1 | 2/2001 | Pineiro et al. |
| 2002/0128477 | A1 | 9/2002 | Zhou et al. |

FOREIGN PATENT DOCUMENTS

| WO | 01/12629 | 2/2001 |
| WO | 02/051837 | 7/2002 |
| WO | 02/060871 | 8/2002 |
| WO | 03/035061 | 5/2003 |
| WO | 03/053970 | 7/2003 |

OTHER PUBLICATIONS

Radl, Stanislav et al. "Synthesis and analgesis activity of some 1-benzofurans, 1-benxothiophenes and indoles," Selection of Czechoslovak Chemical Communications (2000), vol. 65, No. 2, pp. 280-296.*
U.S. Appl. No. 11/679,344, filed Feb. 27, 2007, Merce Vidal.
U.S. Appl. No. 11/673,328, filed Feb. 9, 2007, Merce Vidal et al.

* cited by examiner

*Primary Examiner*—Kamal A Saeed
*Assistant Examiner*—Janet L Coppins
(74) *Attorney, Agent, or Firm*—Oblon, Spivak, McClelland, Maier & Neustadt, L.L.P.

(57) ABSTRACT

The present invention refers to new sulfonamide derivatives, of general formula (Ia, Ib, Ic), (I), (Ia, Ib, Ic), optionally in form of one of their stereoisomers, preferably enantiomers or diastereomers, their racemate, or in form of a mixture of at least two of their stereoisomers, preferably enantiomers or diastereomers, in any mixing ratio, or their salts, preferably their corresponding physiologically acceptable salts or corresponding solvates; to the processes for their preparation, to their application as medicaments in human and/or veterinary therapeutics, and to the pharmaceutical compositions containing them. The new compounds of the present invention can be used in the pharmaceutical industry as intermediates and for preparing medicaments.

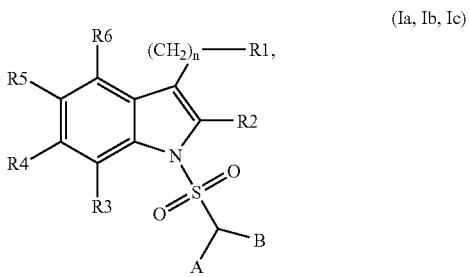

49 Claims, No Drawings

1-SULFONYLINDOLE DERIVATIVES, THEIR PREPARATION AND THEIR USE AS 5-HT$_6$ LIGANDS

The present invention refers to new sulfonamide derivatives, of general formula (Ia, Ib, Ic),

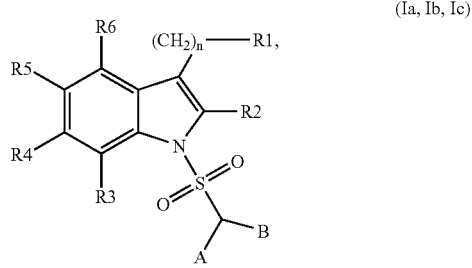

optionally in form of one of their stereoisomers, preferably enantiomers or diastereomers, their racemate, or in form of a mixture of at least two of their stereoisomers, preferably enantiomers or diastereomers, in any mixing ratio, or their salts, preferably their corresponding, physiologically acceptable salts, or corresponding solvates; to the processes for their preparation, to their application as medicaments in human and/or veterinary therapeutics, and to the pharmaceutical compositions containing them.

The new compounds of the present invention can be used in the pharmaceutical industry as intermediates and for preparing medicaments.

The superfamily of serotonin receptors (5-HT) comprises 7 classes (5-HT$_1$-5-HT$_7$), which cover 14 human subclasses [D. Hoyer, et al., *Neuropharmacology*, 1997, 36, 419]. The 5-HT$_6$ receptor has been the last serotonin receptor identified by molecular cloning in rats [F. J. Monsma, et al., *Mol. Pharmacol.*, 1993, 43, 320; M. Ruat, et al., *Biochem. Biophys. Res. Commun.*, 1993, 193, 268] as well as in humans [R. Kohen, et al., *J. Neurochem.*, 1996, 66, 47]. The compounds with an affinity for the 5-HT$_6$ receptor are useful in treating different disorders of the Central Nervous System and of the Gastrointestinal system, as well as the irritable bowel syndrome. The compounds with an affinity for the 5-HT$_6$ receptor are useful for treating anxiety, depression and cognitive memory disorders [M. Yoshioka, et al., Ann. NY Acad. Sci., 1998, 861, 244; A. Bourson, et al., Br. J. Pharmacol., 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that the typical and atypical antipsychotics for treating schizophrenia have a high affinity for the 5-HT$_6$ receptors [B. L. Roth, et al., *J. Pharmacol. Exp. Ther.*, 1994, 268, 1403; C. E. Glaft, et al., *Mol. Med.*, 1995, 1, 398; F. J. Mosma, et al., *Mol. Pharmacol.*, 1993, 43, 320; T. Shinkai, et al, *Am. J. Med. Genet.*, 1999, 88, 120]. The compounds with an affinity for the 5-HT$_6$ receptor are useful for treating infantile hyperkinesia (ADHD, attention deficit/hyperactivity disorder) [W. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379].

Patent application WO 01/32646 discloses sulfonamides derived from bicycles whereby each of the rings is 6-membered, aromatic or heteroaromatic rings with 5-HT$_6$ receptor antagonist activity.

Patent application EP 0 733 628 discloses sulfonamides derived from indole with 5-HT1F receptor antagonist activity, useful for the treatment of migraines.

Furthermore, it has been shown that the 5-HT$_6$ receptor plays a role in the ingestion of food [Neuropharmacology, 41, 2001, 210-219].

Eating disorders, particularly obesity, are a serious and increasingly frequent threat for the health of humans of all ages, since these diseases increase the risk of developing other serious and even mortal diseases, preferably diabetes and coronary artery diseases.

Therefore, an object of the present invention was to provide new compounds, particularly suitable as active substances in medicaments, preferably in medicaments for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans.

It has been found that the 1-sulfonylindole derivatives of general formulas (Ia, Ib, Ic) described below show an affinity for the 5-HT$_6$ receptor.

These compounds are therefore suitable for preparing a medicament for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans. These compounds are also suitable for the preparation of a medicament for cognitive enhancement.

Thus, one aspect of the present invention are compounds of general formula (Ia),

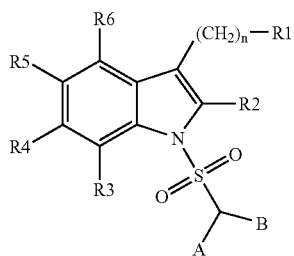

wherein $R^1$ represents a —$NR^7R^8$ radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, $R^2$, $R^3$, $R^4$, $R^5$ and $R^6$, identical or different, each represent hydrogen, halogen, cyano, nitro, a saturated or unsaturated, linear or branched aliphatic radical, a linear or branched alkoxy radical, a linear or branched alkylthio radical, hydroxy, trifluoromethyl, a saturated or unsaturated cycloaliphatic radical, an alkylcarbonyl radical, a phenylcarbonyl or a —$NR^9R^{10}$ group, $R^7$ and $R^8$, identical or different, each represent hydrogen or a saturated or unsaturated, optionally at least mono-substituted linear or branched aliphatic radical, with the proviso that $R^8$ and $R^9$ are not hydrogen at the same time, and if one of them, $R^8$ or $R^9$, is a saturated or unsaturated, linear or branched, optionally at least mono-substituted $C_1$-$C_4$ aliphatic radical, the other one is a saturated or unsaturated, linear or branched, optionally at least mono-substituted aliphatic radical with at least five carbon atoms, or $R^7$ and $R^8$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, $R^9$ and $R^{10}$, identical or different, each represent hydrogen or a saturated or unsaturated, linear or branched, optionally at least mono-substituted aliphatic radical, or $R^9$ and $R_{11}$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, A and B, identical or different, each represent a saturated or unsaturated, linear or branched, optionally at least mono-substituted aliphatic radical or A and B, together with the carbon atom to which they are attached, form a saturated or unsaturated, but not aromatic, optionally at least mono-substituted cycloalkyl ring, and n is 0, 1, 2, 3, or 4, optionally in form of one of their stereoisomers, preferably enantiomers or diastereomers, their racemate or in form of a mixture of at least two of their stereoisomers, preferably enantiomers or diastereomers, in any mixing ratio, or a salt thereof, preferably a corresponding physiologically acceptable salt thereof or a corresponding solvate thereof.

Another aspect of the present invention are compounds of general formula (Ib)

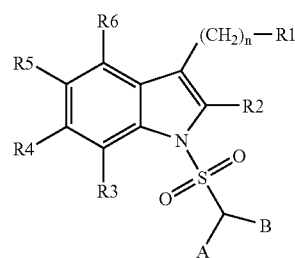

wherein $R^1$ is a —$NR^7R^8$ radical, $R^2$, $R^3$, $R^4$, $R^5$ and $R^6$, identical or different, each represent hydrogen, halogen, cyano, nitro, a saturated or unsaturated, linear or branched aliphatic radical, a linear or branched alkoxy radical, a linear or branched alkylthio radical, hydroxy, trifluoromethyl, a saturated or unsaturated cycloaliphatic radical, an alkylcarbonyl radical, a phenylcarbonyl or a —$NR^9R^{10}$ group, $R^7$ and $R^8$, identical or different, each represent hydrogen or a saturated or unsaturated, optionally at least mono-substituted linear or branched $C_{1-4}$ aliphatic radical, $R^9$ and $R^{10}$, identical or different, each represent hydrogen or a saturated or unsaturated, linear or branched, optionally at least mono-substituted aliphatic radical, or $R^9$ and $R^{10}$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, A and B, identical or different, each represent a saturated or unsaturated, linear or branched, optionally at least mono-substituted aliphatic radical or A and B, together with the carbon atom to which they are attached, form a saturated or unsaturated, but not aromatic, optionally at least mono-substituted cycloalkyl ring, and n is 0, 1, 2, 3 or 4;

optionally in form of one of its stereoisomers, preferably enantiomers or diastereomers, their racemate or in form of a mixture of at least two of their stereoisomers, preferably enantiomers or diastereomers, in any mixing ratio, or a salt thereof, preferably a corresponding physiologically acceptable salt thereof or a corresponding solvate thereof.

Yet, another aspect of the present invention are compounds of general formula (Ic)

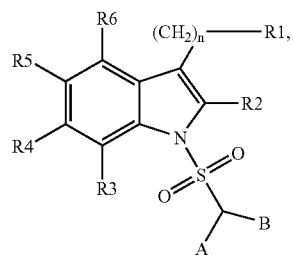
(Ic)

wherein $R^1$ represents a —$NR^7R^8$ radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, $R^2$, $R^3$, $R^4$, $R^5$ and $R^6$, identical or different, each represent hydrogen, halogen, cyano, nitro, a saturated or unsaturated, linear or branched aliphatic radical, a linear or branched alkoxy radical, a linear or branched alkylthio radical, hydroxy, trifluoromethyl, a saturated or unsaturated cycloaliphatic radical, an alkylcarbonyl radical, a phenylcarbonyl or a —$NR^9R^{10}$ group, $R^7$ and $R^8$, identical or different, each represent hydrogen or a saturated or unsaturated, optionally at least mono-substituted linear or branched aliphatic radical, or $R^7$ and $R^8$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, $R^9$ and $R^{10}$, identical or different, each represent hydrogen or a saturated or unsaturated, linear or branched, optionally at least mono-substituted aliphatic radical, or $R^9$ and $R^{10}$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, A and B, identical or different, each represent a saturated or unsaturated, linear or branched, optionally at least mono-substituted aliphatic radical or A and B, together with the carbon atom to which they are bonded, form a saturated or unsaturated, but not aromatic, optionally at least mono-substituted cycloalkyl ring, and n is 0, 1, 2, 3, or 4, optionally in form of one of their stereoisomers, preferably enantiomers or diastereomers, their racemate or in form of a mixture of at least two of their stereoisomers, preferably enantiomers or diastereomers, in any mixing ratio, or a salt thereof, preferably a corresponding physiologically acceptable salt thereof or a corresponding solvate thereof.

If one or more of the moieties $R^2$-$R^{10}$, A and B, represent an alkyl radical, an alkenyl radical or an alkynyl radical, which is substituted by one or more substituents, each one of these substituents can preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy, or an optionally at least mono-substituted phenyl radical.

If said phenyl radical is substituted by one one or more substituents as well, each one of these substituents can preferably be chosen from the group consisting of fluorine, chlorine, bromine, a linear or branched $C_1$-$C_6$ alkyl, a linear or branched $C_1$-$C_6$ alkoxy, a linear or branched $C_1$-$C_6$ alkylthio, a trifluoromethyl radical, a cyano radical and an $NR^{11}R^{12}$ radical, wherein $R^{11}$ and $R^{12}$, identical or different, are defined as $R^7$ and $R^8$.

If $R^1$ is a saturated or unsaturated, optionally at least one heteroatom as a ring member containing cycloaliphatic radical, which is substituted by one or more substituents and/or if $R^1$ comprises a saturated or unsaturated, optionally at least one heteroatom as a ring member containing mono- or bicyclic cycloaliphatic ring system, which is substituted by one or more substituents, each one of these substituents can, unless defined otherwise, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably from the group consisting of linear or branched $C_1$-$C_6$ alkyl and benzyl.

The heteroatoms of the cycloaliphatic radical and/or of the mono- or bicyclic cycloaliphatic ring can, independently from one another, preferably be chosen from the group consisting of nitrogen, sulphur and oxygen, more preferably nitrogen is chosen as a heteroatom.

Said cycloaliphatic radical may contain 0, 1, 2 or 3 heteroatoms chosen from the above mentioned group, preferably it contains 0, 1 or 2 heteroatoms chosen from the above mentioned group.

If $R^7$ and $R^8$ together with the bridging nitrogen form a saturated or unsaturated, optionally at least one further heteroatom as a ring member containing heterocyclic ring, which is substituted by one or more substituents and/or condensed with a saturated or unsaturated, optionally at least one heteroatom as a ring member containing mono- or bicyclic cycloaliphatic ring system, which is substituted by one or more substituents, each one of these substituents can, unless defined otherwise, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably from the group consisting of linear or branched $C_1$-$C_6$ alkyl and benzyl.

If the heterocyclic ring contains one or more additional heteroatoms, and/or if one or both mono- or bicyclic rings contain one or more heteroatoms, these heteroatoms can, independently from one another, preferably be chosen from the group consisting of nitrogen, sulphur and oxygen, more preferably nitrogen is chosen as a heteroatom.

Said heterocyclic ring may contain 0, 1, 2 or 3 additional heteroatoms chosen from the above mentioned group, preferably it contains 0 or 1 heteroatoms chosen from the above mentioned group.

If A is an aliphatic radical, i.e. an alkyl, alkenyl or alkynyl radical, substituted by one or more substituents, each one of these substituents can preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy or an optionally at least mono-substituted phenyl radical.

If said phenyl radical is substituted by one or more substituents as well, each one of these substituents can preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and an $NR^{13}R^{14}$ radical, wherein $R^{13}$ and $R^{14}$, identical or different, are defined as $R^7$ and $R^8$.

If B is an aliphatic radical, i.e. an alkyl radical, an alkenyl radical or an alkynyl radical, which is substituted by one or more substituents, each one of these substituents can preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy, or an optionally at least mono-substituted phenyl radical.

If said phenyl radical is substituted by one or more substituents as well, each one of the substituents can preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a $NR^{15}R^{16}$ radical, wherein $R^{15}$ and $R^{16}$, identical or different, are defined as $R^7$ and $R^8$.

If A and B together with the carbon atom to which they are bonded form a saturated or unsaturated, but not aromatic, cycloalkyl ring, which is substituted by one or more substituents, each one of these substituents can preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy or an optionally at least mono-substituted phenyl radical.

If said phenyl radical is substituted by one or more substituents as well, each one of these substituents can preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a $NR^{17}R^{18}$ radical, wherein $R^{17}$ and $R^{18}$, identical or different, are defined as $R^7$ and $R^8$.

If one of the substituents $R^2$, $R^3$, $R^4$, $R^5$ and $R^6$ represents a linear or branched aliphatic radical, a linear or branched alkoxy radical or a linear or branched alkylthio radical, the carbon chain may have preferably 1-6, more preferably 1-3 carbon atoms.

Those skilled in the art understand that the term "condensed" indicates that the condensed rings share more than one atom. The terms "annulated" or "fused" may also be used for this type of bonding.

Sulfonamide derivatives of general formula (Ia) are preferred, wherein $R^1$ represents a —$NR^7R^8$ radical or a saturated or unsaturated, optionally at least mono-substituted, optionally at least one heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered, more preferably $R^1$ represents a $NR^7R^8$ radical or a radical chosen from the group consisting of

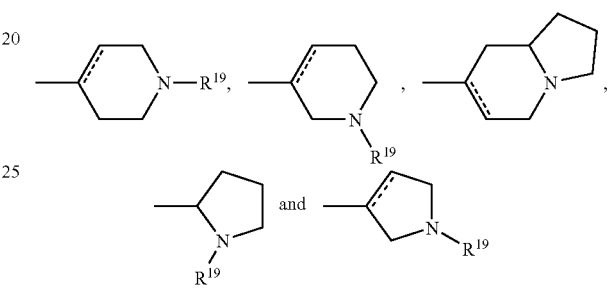

wherein, if present, the dotted line represents an optional chemical bond, and $R^{19}$ represents hydrogen, a linear or branched $C_1$-$C_6$ alkyl radical or a benzyl radical, preferably hydrogen or a $C_1$-$C_2$ alkyl radical and $R^2$-$R^6$, $R^9$, $R^{10}$, A, B and n are defined as above.

Sulfonamide derivatives of general formula (Ia) are also preferred, wherein $R^2$, $R^3$, $R^4$, $R^5$ and $R^6$, identical or different, each represent hydrogen, F, Cl, Br, cyano, nitro, a linear or branched $C_{1-6}$ alkyl radical, a linear or branched $C_{2-6}$ alkenyl radical, a linear or branched $C_{2-6}$ alkynyl radical, a linear or branched $C_{1-6}$ alkoxy, a linear or branched $C_{1-6}$ alkylthio, hydroxy, trifluoromethyl, a saturated or unsaturated $C_{3-8}$ cycloaliphatic radical, a linear or branched $C_{1-6}$ alkylcarbonyl radical, phenylcarbonyl or an —$NR^9R^{10}$ group, more preferably $R^2$, $R^3$, $R^4$, $R^5$ and $R^6$, identical or different, each represent H, F, Cl, $NO_2$, $NH_2$ or a $C_{1-2}$ alkyl radical and $R^1$, $R^7$-$R^{10}$, A, B and n are defined as above.

Furthermore, sulfonamide derivatives of general formula (Ia) are also preferred, wherein $R^7$ and $R^8$, identical or different, each represent hydrogen, a linear or branched, optionally at least mono-substituted $C_{1-10}$ alkyl radical, a linear or branched, optionally at least mono-substituted $C_{2-10}$ alkenyl radical, or a linear or branched, optionally at least mono-substituted $C_{2-10}$ alkynyl radical, with the proviso that $R^8$ and $R^9$ are not hydrogen at the same time, and if one of them, $R^8$ and $R^9$, is a saturated or unsaturated, linear or branched, optionally at least mono-substituted, $C_1$-$C_4$ aliphatic radical, the other one is a saturated or unsaturated, linear or branched, optionally at least mono-substituted aliphatic radical with at least five carbon atoms, or $R^7$ and $R^8$ together with the bridging nitrogen form a saturated or unsaturated, optionally at least mono-substituted, optionally at least one further heteroatom as a ring member containing 5- or 6-membered heterocyclic ring which may be condensed with a saturated or unsaturated, optionally at least mono-substituted, optionally at least one heteroatom as a ring member containing mono- or bicyclic cycloaliphatic ring system, whereby the rings of the ring system are 5- 6- or 7-membered and $R^1$-$R^6$, $R^9$, $R^{10}$, A, B and n are defined as above.

Particularly preferred are sulfonamide derivatives of general formula (Ia), wherein $R^7$ and $R^8$, identical or different, represent hydrogen or a linear or branched $C_1$-$C_{10}$ alkyl radical, with the proviso that $R^8$ and $R^9$ are not hydrogen at the same time, and if one of them, $R^8$ or $R^9$, represents a saturated or unsaturated, linear or branched, optionally at least mono-substituted $C_1$-$C_4$ aliphatic radical, the other one of them represents a saturated or unsaturated, linear or branched, optionally at least mono-substituted aliphatic radical with at least five carbon atoms, or $R^7$ and $R^8$ together with the bridging nitrogen atom form a radical chosen from the group consisting of

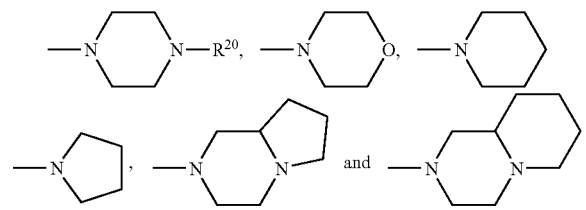

wherein $R^{20}$, if present, represents hydrogen, a linear or branched $C_1$-$C_6$ alkyl radical or a benzyl radical, preferably hydrogen, or a $C_1$-$C_2$ alkyl radical, and $R^1$-$R^6$, $R^9$, $R^{10}$, A, B and n are defined as above.

Furthermore, sulfonamide derivatives of general formula (Ia) are also preferred, wherein $R^9$ and $R^{10}$, identical or different, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical or $R^9$ and $R^{10}$, together with bridging nitrogen atom form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system whereby the rings of the ring system are 5- 6- or 7-membered and $R^1$-$R^8$, A, B and n are defined as above.

Particularly preferred are sulfonamide derivatives of general formula (Ia), wherein $R^9$ and $R^{10}$, identical or different, each represent hydrogen or a linear or branched $C_1$-$C_{10}$ alkyl radical, or $R^9$ and $R^{10}$, together with the bridging nitrogen atom form a radical chosen from the group consisting of

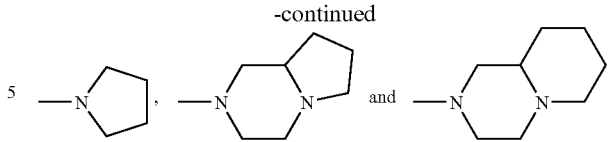

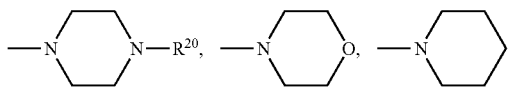

wherein $R^{20}$, if present, represents hydrogen, a linear or branched $C_1$-$C_6$ alkyl radical or a benzyl radical, preferably hydrogen, or a $C_1$-$C_2$ alkyl radical, and $R^1$-$R^8$, A, B and n are defined as above.

Furthermore, sulfonamide derivatives of general formula (Ia) are preferred, wherein A and B, identical or different, each represent a linear or branched $C_1$-$C_6$ alkyl radical, a linear or branched $C_2$-$C_6$ alkenyl radical or a linear or branched $C_2$-$C_6$ alkynyl radical, more preferably A and B, identical or different, each represent a linear or branched $C_1$-$C_6$ alkyl radical, or A and B, together with the carbon atom to which they are bonded, form a saturated or unsaturated, but not aromatic, optionally at least mono-substituted cycloalkyl ring, more preferably A and B together with the carbon atom to which they are bonded form a $C_3$-$C_8$ cycloalkyl ring, even more preferably A and B together with the carbon atom to which they are bonded form a cyclohexyl ring and $R^1$-$R^{10}$ and n are defined as above.

Furthermore sulfonamide derivatives of general formula (Ia) are preferred, wherein n is 0, 1, 2, 3 or 4; preferably n is 0 or 1; more preferably n is 0 and $R^1$ to $R^{10}$ and A and B are defined as above.

Those most preferred compounds of general formula (Ia) are selected from the group consisting of

[1] 1-Cyclohexanesulfonyl-3-(1-methyl-1,2,3,6-tetrahydro-pyridine-4-yl)-5-nitro-1H-indole,

[2] 5-Chloro-1-cyclohexanesulfonyl-3-(1-methyl-1,2,3,6-tetrahydropyridine-4-yl)-1H-indole,

[3] 5-Amino-1-cyclohexanesulfonyl-3-(1-methyl-1,2,3,6-tetrahydropyridine-4-yl)-1H-indole and

[4] 1-Cyclohexanesulfonyl-5-fluoro-3-(1,2,3,5,8,8a-hexahydro-indolizine-7-yl)-1H-indole hydrochloride and their corresponding salts and solvates.

Sulfonamide derivatives of general formula (Ib) are also preferred, wherein $R^2$, $R^3$, $R^4$, $R^5$ and $R^6$, identical or different, each represent hydrogen, F, Cl, Br, cyano, nitro, a linear or branched $C_{1-6}$ alkyl radical, a linear or branched $C_{2-6}$ alkenyl radical, a linear or branched $C_{2-6}$ alkynyl radical, linear or branched $C_{1-6}$-alkoxy, a linear or branched $C_{1-6}$-alkylthio radical, hydroxy, trifluoromethyl, a saturated or unsaturated $C_{3-8}$ cycloaliphatic radical, a linear or branched $C_{1-6}$-alkylcarbonyl radical, phenylcarbonyl or a —$NR^9R^{10}$ group, preferably $R^2$, $R^3$, $R^4$, $R^5$ and $R^6$, identical or different, each represent H, F, Cl, $NO_2$, $NH_2$ or a $C_{1-2}$ alkyl radical, and $R^1$, $R^7$-$R^{10}$, A, B and n are defined as above.

Furthermore, sulfonamide derivatives of general formula (Ib) are also preferred, wherein $R^7$ and $R^8$, identical or different, each represent hydrogen, a linear or branched, optionally at least mono-substituted $C_1$-$C_4$ alkyl radical and $R^1$-$R^6$, $R^9$, $R^{10}$, A, B and n are defined as above.

Particularly preferred are sulfonamide derivatives of general formula (Ib), wherein $R^7$ and $R^8$, identical or different, each represent hydrogen or a $C_1$-$C_2$ alkyl radical, with the proviso that $R^7$ and $R^8$ are not hydrogen at the same time, and $R^1$-$R^6$, $R^9$, $R^{10}$, A, B and n are defined as above.

Furthermore, sulfonamide derivatives of general formula (Ib) are also preferred, wherein $R^9$ and $R^{10}$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical or $R^9$ and $R^{10}$, together with the bridging nitrogen atom form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system whereby the rings of the ring system are 5- 6- or 7-membered and $R^1$-$R^8$, A, B and n are defined as above.

Particularly preferred are sulfonamide derivatives of general formula (Ib), wherein $R^9$ and $R^{10}$, identical or different, each represent hydrogen or a linear or branched $C_1$-$C_{10}$ alkyl radical, or $R^9$ and $R^{10}$, together with the bridging nitrogen form a radical chosen from the group consisting of

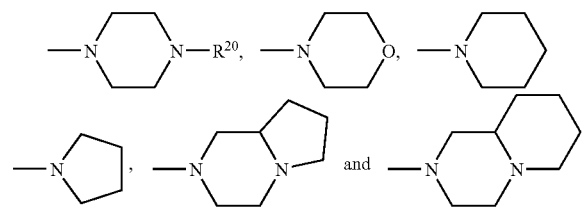

wherein $R^{20}$, if present, represents hydrogen, a linear or branched $C_1$-$C_6$ alkyl radical or a benzyl radical, preferably hydrogen, or a $C_1$-$C_2$ alkyl radical, and $R^1$-$R^8$, A, B and n are defined as above.

Furthermore, sulfonamide derivatives of general formula (Ib) are preferred, wherein A and B, identical or different, each represent a linear or branched $C_1$-$C_6$ alkyl radical, a linear or branched $C_1$-$C_6$ alkenyl radical, or a linear or branched $C_1$-$C_6$ alkynyl radical, preferably a linear or branched $C_1$-$C_6$ alkyl radical, or A and B, together with the carbon atom to which they are bonded, form a saturated or unsaturated, but not aromatic, optionally at least mono-substituted cycloalkyl ring, more preferably A and B together with the carbon atom to which they are bonded form a $C_3$-$C_8$ cycloalkyl ring, even more preferably A and B together with the carbon atom to which they are bonded form a cyclohexyl ring and $R^1$-$R^{10}$ and n are defined as above.

Furthermore sulfonamide derivatives of general formula (Ib) are preferred, wherein n is 0, 1, 2, 3 or 4; preferably n is 0 or 1; more preferably n is 0 and $R^1$ to $R^{10}$ and A and B are defined as above.

Sulfonamide derivatives of general formula (Ic) are preferred, wherein $R^1$ represents a —$NR^7R^8$ radical or a saturated or unsaturated, optionally at least mono-substituted, optionally at least one heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered, more preferably $R^1$ represents a $NR^7R^8$ radical or a radical chosen from the group consisting of

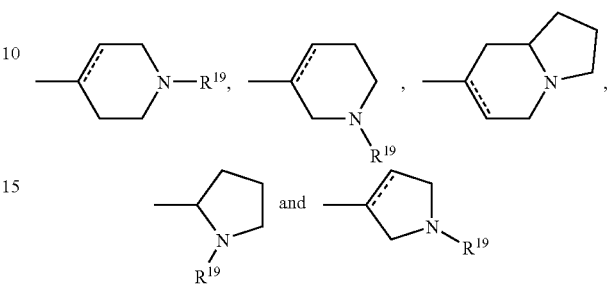

wherein, if present, the dotted line represents an optional chemical bond, and $R^{19}$ represents hydrogen, a linear or branched $C_1$-$C_6$ alkyl radical or a benzyl radical, preferably hydrogen or a $C_1$-$C_2$ alkyl radical and $R^2$-$R^6$, $R^9$, $R^{10}$, A, B and n are defined as above.

Sulfonamide derivatives of general formula (Ic) are also preferred, wherein $R^2$, $R^3$, $R^4$, $R^5$ and $R^6$, identical or different, each represent hydrogen, F, Cl, Br, cyano, nitro, a linear or branched $C_{1-6}$ alkyl radical, a linear or branched $C_{2-6}$ alkenyl radical, a linear or branched $C_{2-6}$ alkynyl radical, a linear or branched $C_{1-6}$ alkoxy, a linear or branched $C_{1-6}$ alkylthio, hydroxy, trifluoromethyl, a saturated or unsaturated $C_{3-8}$ cycloaliphatic radical, a linear or branched $C_{1-6}$ alkylcarbonyl radical, phenylcarbonyl or an —$NR^9R^{10}$ group, more preferably $R^2$, $R^3$, $R^4$, $R^5$ and $R^6$, identical or different, each represent H, F, Cl, $NO_2$, $NH_2$ or a $C_{1-2}$ alkyl radical and $R^1$, $R^7$-$R^{10}$, A, B and n are defined as above.

Furthermore, sulfonamide derivatives of general formula (Ic) are also preferred, wherein $R^7$ and $R^8$, identical or different, each represent hydrogen, a linear or branched, optionally at least mono-substituted $C_{1-10}$ alkyl radical, a linear or branched, optionally at least mono-substituted, $C_{2-10}$ alkenyl radical, or a linear or branched, optionally at least mono-substituted, $C_{2-10}$ alkynyl radical, or $R^7$ and $R^8$ together with the bridging nitrogen form a saturated or unsaturated, optionally at least mono-substituted, optionally at least one further heteroatom as a ring member containing 5- or 6-membered heterocyclic ring which may be condensed with a saturated or unsaturated, optionally at least mono-substituted, optionally at least one heteroatom as a ring member containing mono- or bicyclic cycloaliphatic ring system, whereby the rings of the ring system are 5- 6- or 7-membered and $R^1$-$R^6$, $R^9$, $R^{10}$, A, B and n are defined as above.

Particularly preferred are sulfonamide derivatives of general formula (Ic), where $R^7$ and $R^8$, identical or different, represent hydrogen or a linear or branched $C_1$-$C_{10}$ alkyl radical, or $R^7$ and $R^8$ together with the bridging nitrogen atom form a radical chosen from the group consisting of

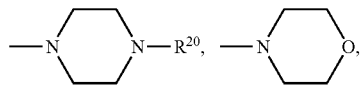

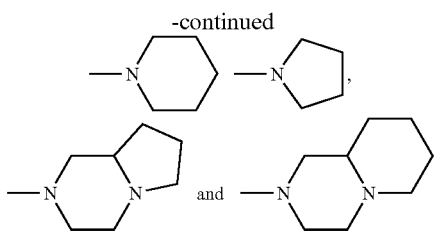

wherein $R^{20}$, if present, represents hydrogen, a linear or branched $C_1$-$C_6$ alkyl radical or a benzyl radical, preferably hydrogen, or a $C_1$-$C_2$ alkyl radical, and $R^1$-$R^6$, $R^9$, $R^{10}$, A, B and n are defined as above.

Furthermore, sulfonamide derivatives of general formula (Ic) are also preferred, wherein $R^9$ and $R^{10}$, identical or different, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical or $R^9$ and $R^{10}$, together with bridging nitrogen atom form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system whereby the rings of the ring system are 5- 6- or 7-membered and $R^1$-$R^8$, A, B and n are defined as above.

Particularly preferred are sulfonamide derivatives of general formula (Ic), wherein $R^9$ and $R^{10}$, identical or different, each represent hydrogen or a linear or branched $C_1$-$C_{10}$ alkyl radical, or $R^9$ and $R^{10}$, together with the bridging nitrogen atom form a radical chosen from the group consisting of

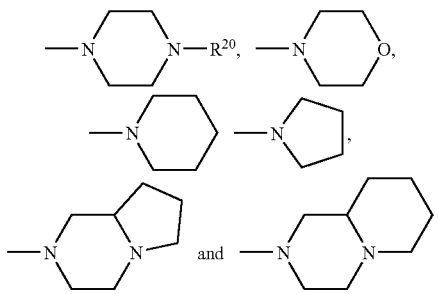

wherein $R^{20}$, if present, represents hydrogen, a linear or branched $C_1$-$C_6$ alkyl radical or a benzyl radical, preferably hydrogen, or a $C_1$-$C_2$ alkyl radical, and $R^1$-$R^8$, A, B and n are defined as above.

Furthermore, sulfonamide derivatives of general formula (Ic) are preferred, wherein A and B, identical or different, each represent a linear or branched $C_1$-$C_6$ alkyl radical, a linear or branched $C_2$-$C_6$ alkenyl radical or a linear or branched $C_2$-$C_6$ alkynyl radical, more preferably A and B, identical or different, each represent a linear or branched $C_1$-$C_6$ alkyl radical, or A and B, together with the carbon atom to which they are bonded, form a saturated or unsaturated, but not aromatic, optionally at least mono-substituted cycloalkyl ring, more preferably A and B together with the carbon atom to which they are bonded form a $C_3$-$C_8$ cycloalkyl ring, even more preferably A and B together with the carbon atom to which they are bonded form a cyclohexyl ring and $R^1$-$R^{10}$ and n are defined as above.

Furthermore sulfonamide derivatives of general formula (Ic) are preferred, wherein n is 0, 1, 2, 3 or 4; preferably n is 0 or 1; more preferably n is 0 and $R^1$ to $R^{10}$ and A and B are defined as above.

Another aspect of the present invention are compounds of general formula (Ic),

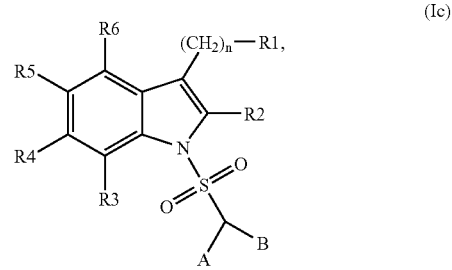

wherein $R^1$ represents an unsaturated, optionally at least one nitrogen atom as a ring member containing 5- or 6-membered cycloaliphatic radical, which may be substituted by a methyl group and/or which may be condensed with a 5-membered cycloaliphatic ring, more preferably $R^1$ represents a —$NR^7R^8$ radical or a moiety selected from the group consisting of

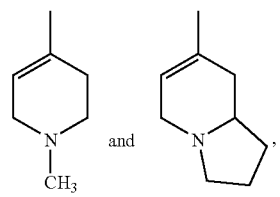

$R^2$, $R^3$, $R^4$ and $R^6$ each represent hydrogen, $R^5$ represents H, fluorine, chlorine, nitro or a —$NR^9R^{10}$ group, $R^9$ and $R^{10}$ each represent hydrogen, A and B together with the carbon atom to which they are bonded form a saturated or unsaturated, but not aromatic, $C_3$-$C_8$ cycloalkyl ring, more preferably form a cyclohexyl ring, and n is 0;

optionally in form of one of their stereoisomers, preferably enantiomers or diastereomers, their racemate or in form of a mixture of at least two of their stereoisomers, preferably enantiomers or diastereomers, in any mixing ratio, or a salt thereof, preferably a corresponding physiologically acceptable salt thereof or a corresponding solvate thereof.

Those most preferred compounds of general formula (Ic) are selected from the group consisting of

[1] 1-Cyclohexanesulfonyl-3-(1-methyl-1,2,3,6-tetrahydropyridine-4-yl)-5-nitro-1H-indole,
[2] 5-Chloro-1-cyclohexanesulfonyl-3-(1-methyl-1,2,3,6-tetrahydropyridine-4-yl)-1H-indole,
[3] 5-Amino-1-cyclohexanesulfonyl-3-(1-methyl-1,2,3,6-tetrahydropyridine-4-yl)-1H-indole and
[4] 1-Cyclohexanesulfonyl-5-fluoro-3-(1,2,3,5,8,8a-hexahydro-indolizine-7-yl)-1H-indole hydrochloride and their corresponding salts and solvates.

The present invention likewise refers to the salts, preferably the physiologically acceptable salts of the compounds of general formula (Ia) and/or (Ib) and/or of general formula (Ic), preferably the addition salts of mineral acids, more preferably of hydrochloric acid, hydrobromic acid acid, phosphoric acid, sulphuric acid, nitric acid, and the salts of organic acids, more preferably of citric acid, maleic acid acid, fumaric acid, tartaric acid or their derivatives, p-toluenesulphonic acid, methanesulphonic acid, camphorsulphonic acid, etc.

Below, the expression sulfonamide derivatives of general formula (I) refers to one or more compounds of general formula (Ia) and/or to one or more compounds of general formula (Ib) and/or to one or more compounds of general formula (Ic), respectively and optionally in form of one of their stereoisomers, preferably enantiomers or diastereomers, their racemate, or in form of a mixture of at least two of their stereoisomers, preferably enantiomers or diastereomers, in any mixing ratio, or a salt thereof, preferably a corresponding physiologically acceptable salt thereof, or a corresponding solvate thereof.

Another aspect of the present invention consists of a process for preparing the new derivatives of general formula (I), wherein $R^1$-$R^{10}$, A, B and n have the previously indicated meaning, according to which at least one compound of general formula (II).

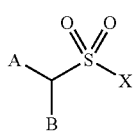
(II)

wherein A and B have the previously mentioned meaning and X is an acceptable leaving group, preferably an halogen atom, more preferably chlorine, is reacted with at least one substituted indole of general formula (III)

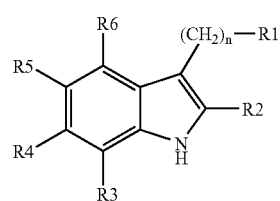
(III)

wherein $R^1$-$R^6$ and n have the previously indicated meaning, or one of their suitable protected derivatives, and, if necessary, the protective groups are removed in order to obtain the corresponding sulfonamide derivative of formula (I), which can be purified and/or isolated by means of conventional methods known in the prior art.

The reaction is preferably carried out in the presence of a suitable strong base, for example, lithium diisopropylamide, butyllithium, sodium hydride, or sodium bis(trimethylsilyl) amide in an inert solvent, preferably tetrahydrofurane, hexane or dimethylformamide. The most suitable reaction temperatures range from −100° C. to room temperature, and the reaction time preferably comprises from 5 minutes to 24 hours. The most preferred conditions are sodium hydride in dimethylformamide at approximately 0° C.

The resulting sulfonamide derivative of general formula (I) can be purified and/or isolated according to conventional methods known in the prior art.

Preferably, the sulfonamide derivatives of general formula (I) can be isolated by evaporating the reaction medium, adding water and, if necessary, adjusting the pH so that a solid which can be isolated by filtration is obtained; or the sulfonamide derivatives can be extracted with a water immiscible solvent, preferably chloroform, and be purified by chromatography or recrystallization of a suitable solvent.

The compounds of general formula (II) are commercially available or can be prepared according to standard methods known in the prior art, for example by methods similar to those described in the literature [KHANNA, V.; TAMILSELVAN, P.; KALRA, S. J. S.; IQBAL, J.; Tetrahedron 1994, 35 (32), 5935-5938; L. N. Aristarkhova et al., *J. Org. Chem.* USSR, 1970, 6, 2454-2458; E. E. Gilbert, *Synthesis*, 1969, 1, 3]. The compounds of general formula (III) can also be prepared according to standard methods known in the prior art, for example, methods similar to those described in the literature. Substituted aromatic 5-HT1f agonist, WO9846570. Piperidine-indole compounds having 5-HT6 affinity, U.S. Pat. No. 6,133,287.

The respective descriptions in the literature are incorporated by reference and form part of the disclosure.

Another aspect of the present invention consists of a process for preparing the new sulfonamide derivatives of general formula (I), wherein one or more of $R^2$, $R^3$, $R^4$, $R^5$ or $R^6$ are reduced to an amino group by reduction of the nitro group of derivatives of general formula (IV) by methods known in the prior art, for example BRATTON, L. D.; ROTH, B. D.; TRIVEDI, B. K.; UNANGST, P. C.; J. Heterocycl Chem, 2000, 37 (5), 1103-1108. FANGHAENEL, E.; CHTCHEGLOV, D.; J Prakt Chem/Chem-Ztg, 1996, 338 (8), 731-737. KUYPER, L. F.; BACCANARI, D. P.; JONES, M. L.; HUNTER, R. N.; TANSIK, R. L.; JOYNER, S. S.; BOYTOS, C. M.; RUDOLPH, S. K.; KNICK, V.; WILSON, H. R.; CADDELL, J. M.; FRIEDMAN, H. S.; ET AL.; J Med Chem, 1996, 39 (4), 892-903,

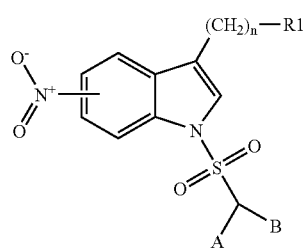
(IV)

and the others $R^1$-$R^6$, A, B and n have the previously mentioned meaning, or one of their derivatives suitably protected, and, if necessary, the protective groups are removed in order to obtain the corresponding amine of general formula (I), which can be purified and/or isolated by means of conventional methods known in the prior art.

The respective literature descriptions are incorporated by reference and form part of the disclosure.

The salts, preferably pharmaceutically acceptable salts of the compounds of general formula (I), may be prepared by means of conventional methods known in the prior art, preferably by reaction with a mineral acid, more preferably by reaction with hydrochloric acid, hydrobromic acid, phosphoric acid acid, sulphuric acid or nitric acid, or by reaction with organic acids, more preferably by reaction with citric acid, maleic acid, fumaric acid acid, tartaric acid, or their derivatives, p-toluenesulphonic acid, methanesulphonic acid, camphorsulphonic acid, etc., in a suitable solvent, preferably methanol, ethanol, diethyl ether, ethyl acetate, acetonitrile or acetone, and obtaining the resulting salts by using the usual techniques for the precipitation or crystallization of the corresponding salts.

The preferred physiologically acceptable salts of the sulfonamide derivatives of general formula (I) are the addition salts of mineral acids, more preferably of hydrochloric acid, hydrobromic acid, phosphoric acid, sulphuric acid acid or nitric acid, and the addition salts of organic acids, more preferably citric acid, maleic acid, fumaric acid, tartaric acid, or their derivatives, p-toluenesulphonic acid, methanesulphonic acid, camphorsulphonic acid, etc.

The solvates, preferably the physiologically acceptable solvates, more preferably hydrates, of the sulfonamide derivatives of general formula (I) or of the corresponding physiologically acceptable salts, may be prepared by methods known in the prior art.

During some of the synthetic sequences described or in the preparation of the suitable reagents used, it may be necessary and/or desirable to protect sensitive or reactive groups in some of the molecules used. This can be carried out by means of the use of conventional protective groups preferably those described in the literature [Protective groups in Organic Chemistry, ed. J. F. W. McOmie, Plenum Press, 1973; T. W. Greene & P. G. M. Wuts, Protective Groups in Organic Chemistry, John Wiley & Sons, 1991]. The protective groups can be removed in the suitable subsequent stage by methods known in the prior art. The respective literature descriptions are incorporated by reference and form part of the disclosure.

If the sulfonamide derivatives of general formula (I) are obtained in form of a mixture of stereoisomers, preferably enantiomers or diastereomers, said mixtures can be separated by means of standard processes known in the prior art, for example chromatographic methods or crystallization with chiral agents.

Another aspect of the present invention is a medicament comprising at least one 1-sulfonylindole derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-$HT_6$ serotonin receptor in humans and/or in animals, preferably in mammals, more preferably in humans.

Another aspect of the present invention is a medicament comprising at least one 1-sulfonylindole derivative of general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-$HT_6$ serotonin receptor in humans and/or in animals, preferably in mammals, more preferably in humans, more suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome in humans and/or in animals, preferably in mammals, more preferably in humans.

Another aspect of the present invention is a medicament comprising at least one 1-sulfonylindole derivative of general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans, more suitable for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) in humans and/or in animals, preferably in mammals, more preferably in humans.

Another aspect of the present invention is a medicament composed of at least one 1-sulfonylindole derivative of general formula (Ic), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans.

The medicament obtained according to the present invention is particularly suitable for the administration to mammals, including humans. The medicament can preferably be administered to all age groups, namely, children, adolescents and adults.

Another aspect of the present invention is the use of at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

Another aspect of the present invention is the use of at least one sulfonamide derivative of the previous general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans, preferably for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome receptor in humans and/or in animals, preferably in mammals, more preferably in humans.

Another aspect of the present invention is the use of at least one sulfonamide derivative of the previous general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans, preferably for the manufacture of a medicament for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) in animals, preferably in mammals, more preferably in humans.

Another aspect of the present invention is the use of at least one sulfonamide derivative of the previous general formula (Ic), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

The preparation of the corresponding pharmaceutical compositions as well as of the formulated medicaments can be carried out by means of conventional methods known in the prior art, for example, based on the indices of "Pharmaceutics: The Science of Dosage Forms", Second Edition, Aulton, M. E. (ED. Churchill Livingstone, Edinburgh (2002)); "Encyclopedia of Pharmaceutical Technology", Second Edition, Swarbrick, J. and Boylan, J. C. (Eds.), Marcel Dekker, Inc. New York (2002); "Modern Pharmaceutics", Fourth Edition, Banker G. S. and Rhodes C. T. (Eds.) Marcel Dekker, Inc. New York (2002), and "The Theory and Practice of Industrial Pharmacy", Lachman L., Lieberman H. and Kanig J. (Eds.), Lea & Febiger, Philadelphia (1986). The respective literature descriptions are incorporated as a reference and are part of this disclosure.

The pharmaceutical compositions, as well as the formulated medicaments prepared according to the present invention, can, in addition to at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, comprise other conventional auxiliary substances known in the prior art, preferably excipients, fillers, solvents, diluents, dyes, coating agents, matrix forming agents and/or binders. As those skilled in the art also know the choice of the auxiliary substances and the amounts thereof depends on the intended administration route, for example, rectal, intravenous, intraperitoneal, intramuscular, intranasal, oral, buccal or topical.

Medicaments suitable for oral administration are, for example, tablets, coated tablets, capsules or multiparticulates, preferably granules or pellets, optionally subjected to compression in tablets, filled in capsules or suspended in solutions, suspensions or suitable liquids.

Medicaments suitable for parenteral, topical or inhalatory administration can preferably be chosen from the group consisting of solutions, suspensions, quickly reconstitutable dry preparations and also sprays.

Medicaments suitable for oral or percutaneous use can release the sulfonamide compounds of general formula (I) in a sustained manner, the preparation of these sustained release medicaments generally being known in the prior art.

The most suitable sustained release forms, as well as the materials and methods for the preparation thereof, are known in the prior art, for example from the indices of "Modified-Release Drug Delivery Technology", Rathbone, M. J, Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York (2000); "Controlled Drug Delivery", Vol. I, Basic Concepts, Bruck, S. D. (Ed.), CRD Press, Inc., Boca Raton (1983), and by Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective literature references are incorporated by reference and form part of the disclosure.

The medicament of the present invention can also have at least one enteric coating, which dissolves according to the pH. As a result of this coating, the medicament can pass through the stomach without dissolving, and the compounds of general formula (I) are only released in the intestinal tract. The enteric coating preferably dissolves at a pH of between 5 and 7.5. The materials and methods suitable for preparing enteric coatings are also known in the prior art.

Typically, the pharmaceutical compositions and the medicaments comprise from 1 to 60% by weight of one or more sulfonamide derivatives of general formula (I), and from 40 to 99% by weight of one or more excipients.

The medicament substance amount to be administered to the patient varies according to the patient's weight, the administration route, the indication and the severity of the disorder. Usually from 1 mg to 2 g of at least one sulfonamide derivative of general formula (I) are administered per patient per day. The total daily dose can be administered to the patient in one or more doses.

Pharmaceutical Methods:

Binding to the 5HT$_6$ Serotonin Receptor

HEK-293 cell membranes expressing the recombinant human 5HT$_6$ receptor were supplied by Receptor Biology. The receptor concentration in said membranes is 2.18 pmol/ mg of protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytryptamine-7 Receptors. *The Journal of Pharmacology and Experimental Therapeutics*, 1994, 268, 1403], with slight modifications. The commercial membrane is diluted (1:40 dilution) with the binding buffer: 50 mM Tris-HCl, 10 mM $MgCl_2$, 0.5 mM EDTA (pH 7.4). The radioligand used is [$^3H$]-LSD at a concentration of 2.7 nM, the final volume being 200 µl. Incubation begins by adding 100 µl of the membrane suspension (≈22.9 µg of membrane protein), and is prolonged for 60 minutes at a temperature of 37° C. Incubation ends by quick filtration in a Harvester Brandel Cell through fiberglass filters of the Scheleicher & Schuell GF 3362 trademark, pretreated with a 0.5% polyethyleneimine solution. The filters are washed three times with three milliliters of 50 mM Tris HCl buffer, pH 7.4. The filters are transferred to vials and 5 ml of Ecoscint H. liquid scintillation cocktail are added to each vial. The vials are left to equilibrate for several hours prior to their counting in a 1414 Wallac Winspectral scintillation counter. The non-specific binding is determined in the presence of 100 µM of serotonin. The assays are carried out in triplicate. The inhibition constants (KI, nM) are calculated by non-linear regression analysis using the EBDA/LIGAND program [Munson and Rodbard, *Analytical Biochemistry*, 1980, 107, 220].

Measurements of Food Ingestion (Behavior Models)

Male W rats (200-270 g) from Harlan, S. A. are used. The rats are acclimatized to the housings during at least 5 days prior to being subjected to any experiment. During this period, the animals are housed (in groups of five) in translucent cages with water and ad libitum food. The animals are adapted to individual housing at least 24 hours prior to the tests.

The acute effect of the sulfonamide derivatives of general formula (I) used experimentally on food ingestion in rats in fasting conditions is determined as follows:

The rats are kept in fasting conditions for 23 hours in their individual cages of origin. After this period, the rats are orally or intraperitoneally treated with a composition comprising a sulfonamide derivative of general formula (I) or a corresponding composition (vehicle) without said sulfonamide derivative. Immediately after this, the rat is left with pre-weighed food; the accumulated food intake is measured after 1, 2, 4 and 6 hours.

Said food ingestion measuring method is also disclosed in the literature (Kask et al., *European Journal of Pharmacology* 414 (2001), 215-224, and Turnbull et al., *Diabetes, Vol.* 51, August, 2002). The respective parts of the descriptions are herein incorporated as a reference, and they form part of the disclosure.

The preparation of new compounds according to the invention is indicated in the following examples. The affinity for the $5HT_6$ serotonin receptor, as well as the galenic formulas applicable to the compounds of the invention, are described. The examples indicated below, given as an illustrative example, should in no way limit the scope of the invention.

EXAMPLES

Example 1

Preparation of 1-Cyclohexanesulfonyl-3-(1-methyl-1,2,3,6-tetrahydropyridine-4-yl)-5-nitro-1H-indole 468 mg (9.8 mMol) of 50% sodium hydride in oil were added at 0° C. to a solution of 1.0 g (3.9 mMol) of 3-(1-methyl-1,2,3,6-tetrahydropyridine-4-yl)-5-nitro-1H-indole in 50 ml of anhydrous dimethylformamide, and the mixture was left to stir for 30 minutes. Then 2.14 g of cyclohexanesulfonyl chloride were added, and the stirring continued for 3 hours at room temperature. Water was added and evaporated to dryness. The resulting crude was treated with sodium bicarbonate and was extracted with chloroform. The organic phase was dried with anhydrous sodium sulfate and evaporated to dryness; the resulting solid was purified by chromatography, obtaining 900 mg (57%) of 1-cyclohexanesulfonyl-3-(1-methyl-1,2,3,6-tetrahydropyridine-4-yl)-5-nitro-1H-indole as a yellow solid.

Example 2

5-Chloro-1-cyclohexanesulfonyl-3-(1-methyl-1,2,3,6-tetrahydropyridine-4-yl)-1H-indole 900 mg (74%) of the mentioned compound were obtained from 770 mg (3.12 mMol) of 5-chloro-3-(1-methyl-1,2,3,6-tetrahydropyridine-4-yl)-1H-indole, and 1.7 g (9.36 mMol) of cyclohexanesulfonyl chloride by means of the process described in Example 1, as a yellow solid.

Example 3

5-Amino-1-cyclohexanesulfonyl-3-(1-methyl-1,2,3,6-tetrahydropyridine-4-yl)-1H-indole 200 mg of 50% Pd/C with a humidity of 5% were added to a solution of 403 mg (1 mMol) of 1-cyclohexanesulfonyl-3-(1-methyl-1,2,3,6-tetrahydropyridine-4-yl)-5-nitro-1H-indole in 200 ml of ethanol. The resulting suspension was hydrogenized at 25 psi of overpressure for 20 hours. Then the catalyst was filtered and evaporated to drying. The resulting crude was purified by chromatography and 150 mg (40%) of the mentioned compound were obtained as a solid cream.

Example 4

Preparation of 1-Cyclohexanesulfonyl-5-fluoro-3-(1,2,3,5,8,8a-hexahydro-indolizine-7-yl)-1H-indole 1.95 g (78%) of 1-cyclohexanesulfonyl-5-fluoro-3-(1,2,3,5,8,8a-hexahydro-indolizine-7-yl)-1H-indole were obtained as an oil from 1.6 g (6.25 mMol) of 5-fluoro-3-(1,2,3,5,8,8a-hexahydro-indolizine-7-yl)-1H-indole and 3.42 g (18.76 mMol) of cyclohexanesulfonyl chloride by means of the process described in Example 1. Then 2 ml of a 6N ethanol/HCl solution were added to a solution of 1.95 g (4.85 mMol) of 1-cyclohexanesulfonyl-5-fluoro-3-(1,2,3,5,8,8a-hexahydro-indolizine-7-yl)-1H-indole in 20 ml of ethanol, precipitating a solid which was recrystallized from ethanol, obtaining 1.5 g (71%) of the mentioned compound as a white solid.

The yields are indicative and no added effort was made to improve them.

The melting point and spectroscopic data for identifying some of the compounds of the present invention are indicated in the following table.

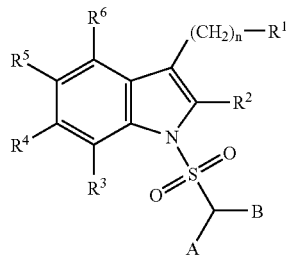

| Ex | R1 | R2 | R3 | R4 | R5 | R6 | n | A | B | Salt | m.p. °C | IR cm⁻¹ | ¹H-NMR (300 MHz), δ(solvent) |
|---|---|---|---|---|---|---|---|---|---|---|---|---|---|
| 1 | —⟨N-CH₃⟩ | H | H | H | NO₂ | H | 0 | cyclohexyl | | — | 155-160 | 3433, 2938, 2859, 1522, 1371, 1340, 1158, 1126, 988, 612. | 1.00-1.90 (m, 10H); 2.56 (s, 3H); 2.68 (m, 2H); 2.98 (m, 2H); 3.47 (m, 2H); 3.78 (m, 1H); 6.35 (s, 1H); 7.87 (s, 1H); 8.08 (d, 1H, J=9.2 Hz); 8.26 (dd, 1H, J=9.2 Hz, J'=1.9 Hz); 8.69 (d, 1H, J=1.8 Hz). (DMSO-d6) |
| 2 | —⟨N-CH₃⟩ | H | H | H | Cl | H | 0 | cyclohexyl | | — | 88-90 | 3433, 2941, 2858, 2787, 1447, 1364, 1158, 1128, 1116, 614, 557. | 1.00-1.90 (m, 10H); 2.41 (s, 3H); 2.55 (m, 2H); 2.67 (m, 2H); 3.15 (m, 3H); 6.18 (m, 1H); 7.27 (dd, 1H, J=8.9 Hz, J'=2.0 Hz); 7.32 (s, 1H); 7.79 (d, 1H, J=2.0 Hz); 7.82 (d, 1H, J=1.8 Hz). (CDCl₃) |
| 3 | —⟨N-CH₃⟩ | H | H | H | NH₂ | H | 0 | cyclohexyl | | — | 75 (decomposition) | 3376, 2937, 2857, 2784, 1455, 1363, 1342, 1158, 1127, 987, 617, 565. | 1.00-1.90 (m, 10H); 2.40 (s, 3H); 2.54 (m, 2H); 2.66 (m, 2H); 3.13 (m, 3H); 6.16 (m, 1H); 6.71 (dd, 1H, J=8.8 Hz, J'=2.4 Hz); 7.09 (d, 1H, J=2.2 Hz); 7.23 (s, 1H); 7.67 (d, 1H, J=8.8 Hz). (CDCl₃) |
| 4 | indolizine | H | H | H | F | H | 0 | cyclohexyl | | HCl | 263 (decomposition) | 3424, 2941, 2499, 2451, 1466, 1445, 1371, 1348, 1188, 1157, 1127, 649, 619. | 1.18 (m, 3H); 1.38 (m, 2H); 1.54 (m, 1H); 1.73 (m, 5H); 2.01 (m 2H); 2.31 (m, 1H); 2.80 (m, 1H); 3.09 (m, 2H); 3.44 (m, 1H); 3.68 (m, 2H); 1H); 7.28 (m, 1H); 7.78 (m, 2H); 7.90 (dd, 1H, J=9.0 Hz, J'=4.6 Hz); (DMSO-d6) |

Pharmaceutical Particulars:

Binding of the new compounds of general formula (I) to the 5-HT₆ receptor was determined as previously described.

The binding results for some of the compounds of the present invention are indicated in the following table:

TABLE

| Example | % Inhibition 10⁻⁶ M | $K_i$ (nM) |
|---|---|---|
| 1 | 59.8 ± 3.0 | |
| 2 | | 98.2 |
| 3 | | 55.1 |
| 4 | | 191 |

The daily posology in human medicine is comprised between 1 milligram and 2 grams of medicinal product which can be administered in one or several doses. The compositions are prepared under forms that are compatible with the administration route used, preferably tablets, coated tablets, capsules, suppositories, solutions or suspensions. These compositions are prepared by means of known methods and comprise from 1 to 60% by weight of the medicament substance (compound of general formula I), and 40 to 99% by weight of the suitable pharmaceutical vehicle compatible with the medicament substance and the physical form of the composition used. The formula of a tablet containing a product of the invention is provided by way of example:

Example of Formula Per Tablet

| | |
|---|---|
| Example 1 | 5 mg |
| Lactose | 60 mg |
| Crystalline cellulose | 25 mg |
| Povidone K 90 | 5 mg |
| Pregelatinized starch | 3 mg |
| Colloidal silicon dioxide | 1 mg |
| Magnesium stearate | 1 mg |
| Total weight per tablet | 100 mg |

The invention claimed is:

1. A sulfonamide of general formula (Ia),

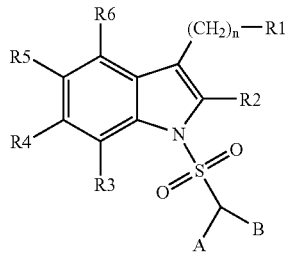

wherein

R[1] represents a —NR[7]R[8] radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, R[2], R[3], R[4], R[5] and R[6], identical or different, each represent hydrogen, halogen, cyano, nitro, a saturated or unsaturated, linear or branched aliphatic radical, a linear or branched alkoxy radical, a linear or branched alkylthio radical, hydroxy, trifluoromethyl, a saturated or unsaturated cycloaliphatic radical, an alkylcarbonyl radical, a phenylcarbonyl or a —NR[9]R[10] group, R[7] and R[8], identical or different, each represent hydrogen or a saturated or unsaturated, optionally at least mono-substituted linear or branched aliphatic radical, with the proviso that R[8] and R[9] are not hydrogen at the same time, and if one of them, R[8] or R[9], is a saturated or unsaturated, linear or branched, optionally at least mono-substituted $C_1$-$C_4$ aliphatic radical, the other one is a saturated or unsaturated, linear or branched, optionally at least mono-substituted aliphatic radical with at least five carbon atoms, or R[7] and R[8], together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, R[9] and R[10], identical or different, each represent hydrogen or a saturated or unsaturated, linear or branched, optionally at least mono-substituted aliphatic radical, or R[9] and R[10], together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, A and B, identical or different, each represent a saturated or unsaturated, linear or branched aliphatic radical, optionally at least mono-substituted or A and B, together with the carbon atom to which they are bonded, form a saturated or unsaturated, but not aromatic cycloalkyl ring, optionally at least mono-substituted and n is 0, or a pharmaceutically acceptable salt thereof.

2. The compound according to claim 1, wherein R[1] represents a —NR[7]R[8] radical or a saturated or unsaturated, optionally at least mono-substituted, optionally at least one heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered.

3. The compound according to claim 1 wherein R[2], R[3], R[4], R[5] and R[6], identical or different, each represent hydrogen, F, Cl, Br, cyano, nitro, a linear or branched $C_{1-6}$ alkyl radical, a linear or branched $C_{2-6}$ alkenyl radical, a linear or branched $C_{2-6}$ alkynyl radical, a linear or branched $C_{1-6}$ alkoxy, a linear or branched $C_{1-6}$ alkylthio, hydroxy, trifluoromethyl, a saturated or unsaturated $C_{3-8}$ cycloaliphatic radical, a linear or branched 1-6 alkylcarbonyl radical, phenylcarbonyl or an —NR[9]R[10] group.

4. The compound according to claim 1, wherein R[7] and R[8], identical or different, each represent hydrogen, a linear or branched, optionally at least mono-substituted $C_{1-10}$ alkyl radical, a linear or branched, optionally at least mono-substituted, $C_{2-10}$ alkenyl radical, or a linear or branched, optionally at least mono-substituted, $C_{2-10}$ alkynyl radical or R[7] and R[8], together with the bridging nitrogen form a saturated or unsaturated, optionally at least mono-substituted, optionally at least one further heteroatom as a ring member containing 5- or 6-membered heterocyclic ring which may be condensed with a saturated or unsaturated, optionally at least mono-substituted, optionally at least one heteroatom as a ring member containing mono- or bicyclic cycloaliphatic ring system, whereby the rings of the ring system are 5- 6- or 7-membered.

5. The compound according to claim 4, wherein R[7] and R[8], identical or different, each represent hydrogen or a linear or branched $C_{1-10}$ alkyl radical or R[7] and R[8], together with the bridging nitrogen atom form a radical chosen from the group consisting of

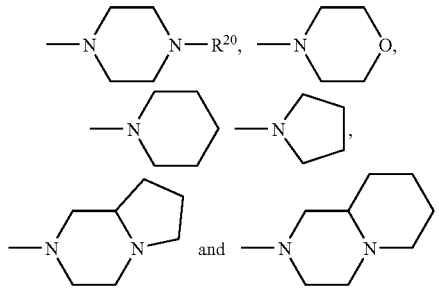

wherein R[20], if present, is hydrogen, a linear or branched $C_1$-$C_6$ alkyl radical or a benzyl radical.

6. The compound according to claim 1, wherein R[9] and R[10], identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical or $R^9$ and $R^{10}$, together with the bridging nitrogen atom form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system whereby the rings of the ring system are 5- 6- or 7-membered.

7. The compound according to claim 6, wherein $R^9$ and $R^{10}$, identical or different, each represent hydrogen or a linear or branched 1-$C_{10}$ alkyl radical, or $R^9$ and $R^{10}$, together with the bridging nitrogen atom form a radical chosen from a group consisting of

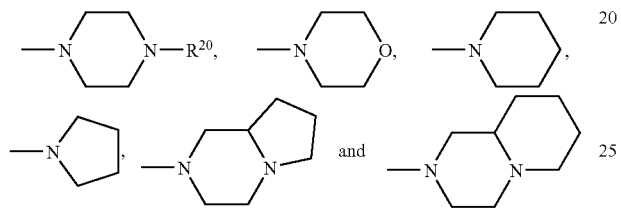

wherein $R^{20}$, if present, is hydrogen, a linear or branched $C_1$-$C_6$ alkyl radical or a benzyl radical.

8. The compound according to claim 1, wherein A and B, identical or different, each represent a linear or branched $C_1$-$C_6$ alkyl radical, a linear or branched $C_2$-$C_6$ alkenyl radical or a linear or branched $C_2$-$C_6$ alkynyl radical, or A and B, together with the carbon atom to which they are bonded, form a saturated or unsaturated, but not aromatic, optionally at least mono-substituted cycloalkyl ring.

9. The compound to claim 1, which is selected from a group consisting of

[1] 1-Cyclohexanesulfonyl-3-(1-methyl-1,2,3,6-tetrahydropyridine-4-yl)-5-nitro-1H-indole,

[2] 5-Chloro-1-cyclohexanesulfonyl-3-(1-methyl-1,2,3,6-tetrahydropyridine-4-yl)-1H-indole,

[3] 5-Amino-1-cyclohexanesulfonyl-3-(1-methyl-1,2,3,6-tetrahydropyridine-4-yl)-1H-indole,

[4] 1-Cyclohexanesulfonyl-5-fluoro-3-(1,2,3,5,8,8a-hexahydro-indolizine-7-yl)-1H-indole hydrochloride, a salt thereof, and a solvate thereof.

10. A sulfonamide compound of general formula (Ib),

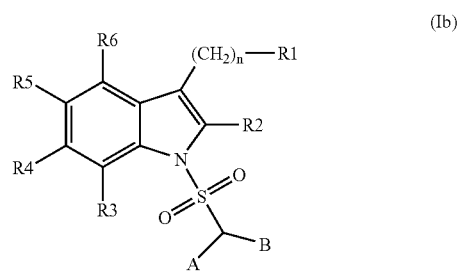

wherein
$R^1$ is a —$NR^7R^8$ radical, $R^2$, $R^3$, $R^4$, $R^5$ and $R^6$, identical or different, each represent hydrogen, halogen, cyano, nitro, a saturated or unsaturated, linear or branched aliphatic radical, a linear or branched alkoxy radical, a linear or branched alkylthio radical, hydroxy, trifluoromethyl, a saturated or unsaturated cycloaliphatic radical, an alkylcarbonyl radical, a phenylcarbonyl or a —$NR^9R^{10}$ group, $R^7$ and $R^8$, identical or different, each represent hydrogen or a saturated or unsaturated, optionally at least mono-substituted linear or branched $C_{1-4}$ aliphatic radical, $R^9$ and $R^{10}$ identical or different, each represent hydrogen or a saturated or unsaturated, linear or branched, optionally at least mono-substituted aliphatic radical, or $R^9$ and $R^{10}$, together with the bridging nitrogen atom form a saturated or unsaturated, optionally at least mono-substituted, optionally at least one further heteroatom as a ring member containing heterocyclic ring which may be condensed with a saturated or unsaturated, optionally at least mono-substituted, optionally at least one heteroatom as a ring member containing mono- or bicyclic cycloaliphatic ring system, A and B, identical or different, each represent a saturated or unsaturated, linear or branched, optionally at least mono-substituted aliphatic radical or A and B, together with the carbon atom to which they are bonded, form a saturated or unsaturated, but not aromatic, optionally at least mono-substituted cycloalkyl ring, and n is 0;

a stereoisomer thereof, an enantiomer thereof, a diastereomer thereof, a racemate thereof, a pharmaceutically acceptable salt thereof, or mixtures thereof.

11. The compound according to claim 10, wherein $R^2$, $R^3$, $R^4$, $R^5$ and $R^6$, identical or different, each represent hydrogen, F, Cl, Br, cyano, nitro, a linear or branched $C_1$-$C_6$ alkyl radical, a linear or branched $C_2$-$C_6$ alkenyl radical, a linear or branched $C_2$-$C_6$ alkynyl radical, a linear or branched $C_1$-$C_6$-alkoxy, a linear or branched $C_1$-$C_6$-alkylthio, hydroxy, trifluoromethyl, a saturated or unsaturated $C_3$-$C_8$ cycloaliphatic radical, a linear or branched $C_1$-$C_6$-alkylcarbonyl radical, phenylcarbonyl or an —$NR^9R^{10}$ group.

12. The compound according to claim 10, wherein $R^7$ and $R^8$, identical or different, wherein $R^7$ and $R^8$, identical or different, each represent hydrogen, a linear or branched, optionally at least mono-substituted $C_1$-$C_4$ alkyl radical with the proviso that $R^7$ and $R^8$ are not hydrogen at the same time.

13. The compound according to claim 10, characterized in that $R^9$ and $R^{10}$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, or a linear or branched, optionally at least mono-substituted $C_2$-$C_{10}$ alkynyl radical or $R^9$ and $R^{10}$, together with the bridging nitrogen atom form a saturated or unsaturated, optionally at least mono-substituted, optionally at least one further heteroatom as a ring member containing 5- or 6-membered heterocyclic which may be condensed with a saturated or unsaturated, optionally at least mono-substituted, optionally at least one heteroatom as a ring member containing mono- or bicyclic cycloaliphatic ring system, whereby the rings of the ring system are 5- 6- or 7-membered.

14. The compound according to claim 13, wherein $R^9$ and $R^{10}$, identical or different, each represent hydrogen or a linear or branched $C_1$-$C_{10}$ alkyl radical, or $R^9$ and $R^{10}$, together with the bridging nitrogen atom form a radical chosen from a group consisting of

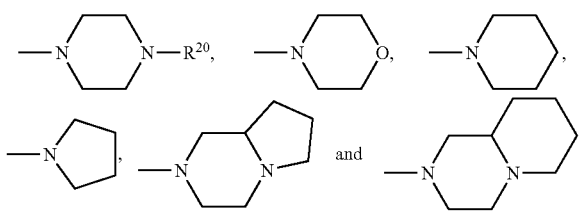

wherein $R^{20}$, if present, represents hydrogen, a linear or branched $C_1$-$C_6$ alkyl radical or a benzyl radical.

15. The compound according to claim 10, wherein A and B, together with the carbon atom to which they are bonded, form a saturated or unsaturated, but not aromatic, optionally at least mono-substituted cycloalkyl ring.

16. A process for obtaining a sulfonamide compound of general formula (Ia) according to claim 1, wherein at least one compound of general formula (II), or a protected compound thereof,

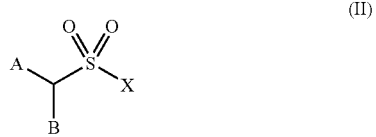 (II)

wherein A and B have the meaning according to claim 1 and X is a leaving group, is reacted with at least one substituted indole of general formula (III)

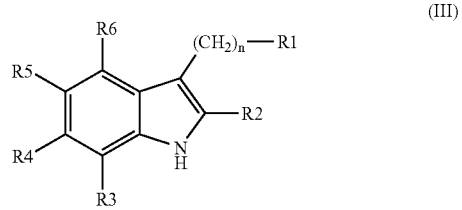 (III)

wherein $R^1$-$R^6$ and n have the meaning according to claim 1, or a protected compound thereof, and, if necessary, the protective groups are removed.

17. A process for obtaining a sulfonamide compound of general formula (Ia) according to claim 1, wherein one or more substituents $R^2$, $R^3$, $R^4$, $R^5$ or $R^6$ represent a nitro group, and wherein a sulfonamide compound of general formula (Ia) is reduced to a sulfonamide compound of corresponding general formula (Ia), wherein one or more substituents $R^2$, $R^3$, $R^4$, $R^5$ or $R^6$ represent an amino group.

18. A process for preparing a salt of the compound of formula (Ia) according to claim 1, the process comprising reacting at least one compound of the general formula (Ia) with a mineral acid or organic acid in a solvent to form the salt of the compound of formula (Ia).

19. A composition comprising at least one compound according to claim 1 and one or more pharmacologically acceptable excipients.

20. A method of treating a disorder or disease related to food intake in a subject in need thereof, the method comprising administering at least one compound according to claim 1 in an amount sufficient to treat the disorder or disease in the subject.

21. A method for regulating appetite in a subject in need thereof, the method comprising administering at least one compound according to claim 1 in an amount sufficient to regulate appetite in the subject.

22. A method for regulating body weight in a subject in need thereof, the method comprising administering at least one compound according to claim 1 in an amount sufficient to regulate body weight in the subject.

23. A method of treating obesity in a subject in need thereof, the method comprising administering at least one compound according to claim 1 in an amount sufficient to treat obesity in the subject.

24. A method of treating bulimia in a subject in need thereof, the method comprising administering at least one compound according to claim 1 in an amount sufficient to treat bulimia in the subject.

25. A method for treating anorexia in a subject in need thereof, the method comprising administering at least one compound according to claim 1 in an amount sufficient to treat anorexia in the subject.

26. A method for treating cachexia in a subject in need thereof, the method comprising administering at least one compound according to claim 1 in an amount sufficient to treat cachexia in the subject.

27. A method for treating type II diabetes in a subject in need thereof, the method comprising administering at least one compound according to claim 1 in an amount sufficient to treat type II diabetes in the subject.

28. A method of treating a gastrointestinal tract disorder in a subject in need thereof, the method comprising administering at least one compound according to claim 1 in an amount sufficient to treat the disorder in the subject.

29. A method for treating irritable bowel syndrome in a subject in need thereof, the method comprising administering at least one compound according to claim 1 in an amount sufficient to treat irritable bowel syndrome in the subject.

30. A method for treating anxiety in a subject in need thereof, the method comprising administering at least one compound according to claim 1 in an amount sufficient to treat anxiety in the subject.

31. A method for treating depression in a subject in need thereof, the method comprising administering at least one compound according to claim 1 in an amount sufficient to treat depression in the subject.

32. A method for treating bipolar disorder in a subject in need thereof, the method comprising administering at least one compound according to claim 1 in an amount sufficient to treat the disorder in the subject.

33. A method for treating infantile hyperkinesia in a subject in need thereof, the method comprising administering at least one compound according to claim 1 in an amount sufficient to treat infantile hyperkinesia in the subject.

34. A method of treating a disorder or disease related to food intake in a subject in need thereof, the method comprising administering at least one compound according to claim 10 in an amount sufficient to treat the disorder or disease in the subject.

35. A method for regulating appetite in a subject in need thereof, the method comprising administering at least one compound according to claim 10 in an amount sufficient to regulate appetite in the subject.

36. A method for regulating body weight in a subject in need thereof, the method comprising administering at least one compound according to claim 10 in an amount sufficient to regulate body weight in the subject.

37. A method of treating obesity in a subject in need thereof, the method comprising administering at least one compound according to claim 10 in an amount sufficient to treat obesity in the subject.

38. A method of treating bulimia in a subject in need thereof, the method comprising administering at least one compound according to claim 10 in an amount sufficient to treat bulimia in the subject.

39. A method for treating anorexia in a subject in need thereof, the method comprising administering at least one compound according to claim 10 in an amount sufficient to treat anorexia in the subject.

40. A method for treating cachexia in a subject in need thereof, the method comprising administering at least one compound according to claim 10 in an amount sufficient to treat cachexia in the subject.

41. A method for treating type II diabetes in a subject in need thereof, the method comprising administering at least one compound according to claim 10 in an amount sufficient to treat type II diabetes in the subject.

42. A method of treating a gastrointestinal tract disorder in a subject in need thereof, the method comprising administering at least one compound according to claim 10 in an amount sufficient to treat the disorder in the subject.

43. A method for treating irritable bowel syndrome in a subject in need thereof, the method comprising administering at least one compound according to claim 10 in an amount sufficient to treat irritable bowel syndrome in the subject.

44. A method for treating anxiety in a subject in need thereof, the method comprising administering at least one compound according to claim 10 in an amount sufficient to treat anxiety in the subject.

45. A method for treating depression in a subject in need thereof, the method comprising administering at least one compound according to claim 10 in an amount sufficient to treat depression in the subject.

46. A method for treating bipolar disorder in a subject in need thereof, the method comprising administering at least one compound according to claim 10 in an amount sufficient to treat the disorder in the subject.

47. A method for treating infantile hyperkinesia in a subject in need thereof, the method comprising administering at least one compound according to claim 10 in an amount sufficient to treat infantile hyperkinesia in the subject.

48. The compound according to claim 1, wherein $R^1$ represents a $-NR^7R^8$ radical or a radical chosen from the group consisting of

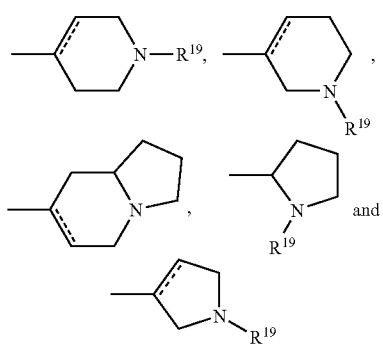

wherein, if present, the dotted line represents an optional chemical bond, and $R^{19}$ represents hydrogen, a linear or branched $C_1$-$C_6$ alkyl radical or a benzyl radical, preferably hydrogen or a $C_1$-$C_2$ alkyl radical.

49. The compound according to claim 1, wherein $R^2$, $R^3$, $R^4$, $R^5$ and $R^6$, identical or different, each represent H, F, Cl, $NO_2$, $NH_2$ or a $C_{1-2}$ alkyl radical.

* * * * *

UNITED STATES PATENT AND TRADEMARK OFFICE
CERTIFICATE OF CORRECTION

| | | |
|---|---|---|
| PATENT NO. | : 7,655,690 B2 | Page 1 of 1 |
| APPLICATION NO. | : 10/566400 | |
| DATED | : February 2, 2010 | |
| INVENTOR(S) | : Merce Vidal et al. | |

It is certified that error appears in the above-identified patent and that said Letters Patent is hereby corrected as shown below:

On the title page, Item (30), the Foreign Application Priority Data is incorrect. Item (30) should read:

-- (30)    Foreign Application Priority Data

July 30, 2003    (ES).................................. P 2003 01806 --

Signed and Sealed this

Thirtieth Day of March, 2010

David J. Kappos
*Director of the United States Patent and Trademark Office*